(12) United States Patent
Akiyama et al.

(10) Patent No.: US 6,943,195 B2
(45) Date of Patent: Sep. 13, 2005

(54) CYCLOALKENONE DERIVATIVE

(75) Inventors: Toshihiko Akiyama, Saitama (JP); Shinji Ina, Saitama (JP); Akane Takahama, Saitama (JP)

(73) Assignee: Nikken Chemicals Co., Ltd, Tokyo (JP)

( * ) Notice: Subject to any disclaimer, the term of this patent is extended or adjusted under 35 U.S.C. 154(b) by 0 days.

(21) Appl. No.: 10/481,060

(22) PCT Filed: Jun. 27, 2002

(86) PCT No.: PCT/JP02/06520

§ 371 (c)(1),
(2), (4) Date: Dec. 16, 2003

(87) PCT Pub. No.: WO03/002511

PCT Pub. Date: Jan. 9, 2003

(65) Prior Publication Data

US 2004/0157933 A1 Aug. 12, 2004

(30) Foreign Application Priority Data

Jun. 29, 2001 (JP) ........................................ 2001-199488

(51) Int. Cl.⁷ ..................... A61K 31/135; C07C 211/00; C07C 43/20
(52) U.S. Cl. ........................ 514/647; 564/428; 564/431; 564/433; 568/636
(58) Field of Search ................................ 564/428, 431, 564/433; 514/647; 568/636

(56) References Cited

FOREIGN PATENT DOCUMENTS

| EP | 0 994 100 A1 | 4/2000 |
| JP | 3-173871 | 7/1991 |
| JP | 8-56693 | 3/1996 |
| JP | 11-189577 | 7/1999 |

OTHER PUBLICATIONS

International Search Report of PCT/JP02/06520, dated Oct. 29, 2002.
International Preliminary Examination Report of PCT/JP02/06520, dated Sep. 9, 2003.
Patent Abstract of Japan, Publication No. 11189577 A, Published on Jul. 13, 1999, in the name of Ine, et al.
Trends Pharmacol. Sci., 12, 19–27 (1992) On Order.
Nicholson, et al., "Differential modulation of tissue function and therapeutic potential of selective inhibitors of cyclic nucleotide phosphodiesterase isoenzymes" TiPS–01–1991, vol. 12, pp. 19–27, Elsevier Science Publishers Ltd. (UK).
Patent Abstract of Japan, Publication 03173871 A, dated Jul. 29, 1991, in the name of Saccomano.
Patent Abstract of Japan, publication 08056693 A, dated Mar. 5, 1996, in the name of Yano, et al.

*Primary Examiner*—Cecilia J. Tsang
*Assistant Examiner*—Taylor Victor Oh
(74) *Attorney, Agent, or Firm*—Christie, Parker & Hale, LLP

(57) ABSTRACT

(−)-3-[3-[(1R,2R,4S)-bicyclo[2.2.1]hept-2-yloxy]-4-methoxyanilino]-2-methyl-2-cyclopenten-1-one, or its hydrate or solvate, or a pharmaceutical composition containing the same.

11 Claims, No Drawings

CYCLOALKENONE DERIVATIVE

CROSS-REFERENCE TO RELATED APPLICATION

This application is a National Phase Patent Application of International Application Number PCT/JP02/06520, filed on Jun. 27, 2002, which claims priority of Japanese Patent Application Number 2001-199488, filed on Jun. 29, 2001.

TECHNICAL FIELD

The present invention relates to a novel compound having a phosphodiesterase (PDE) IV inhibitory activity and a pharmaceutical composition containing the same.

BACKGROUND ART (±)-3-[3-[(1RS,2RS,4SR)-bicyclo[2.2.1]hept-2-yloxy]-4-methoxyanilino]-2-methyl-2-cyclopenten-1-one is known to have a strong PDE IV inhibitory activity and to exhibit a bronchodilating and anti-inflammatory activity (see, for example, Japanese Unexamined Patent Publication (Kokai) No. 11-189577) and is considered effective for inflammatory diseases such as asthma, dermatitis, autoimmune diseases such as rheumatism, multiple sclerosis, etc.

DISCLOSURE OF THE INVENTION (±)-3-[3-[(1RS,2RS,4SR)-bicyclo[2.2.1]hept-2-yloxy]-4-methoxyanilino]-2-methyl-2-cyclopenten-1-one is a racemate (specific rotation of 0°) and has asymmetric carbon at the 1-position, 2-position and 4-position of the bicycloheptyl moiety thereof. The existence of two types of isomers, that is, the (+)-isomer and (−)-isomer, had been predicted, but no general method was established for separation of each isomer of the compound of this structure and separation of each isomer from the racemate could not be achieved.

Further, in the case of the above compound, only the bicycloheptyl moiety has asymmetric carbon. Therefore, the optically active isomers of the compound can be produced by, for example, the method described in Japanese Unexamined Patent Publication (Kokai) No. 11-189577 using optically active endo-norborneols. The method for obtaining optically active endo-norborneols ((+)-(2R)-endo-norborneol and (−)-(2S)-endo-norborneol) is already disclosed in Japanese unexamined Patent Publication (Kokai) No. 3-173871 and Japanese Unexamined Patent Publication (Kokai) No. 8-56693. However, these publications do not describe that the optical isomers are obtained in high purities (95% e.e. or more). According to the description of Japanese Unexamined Patent Publication (Kokai) No. 3-173871, (+)-(2R)-endo-norborneol is obtained in high purity (95% e.e. or more), but (−)-(2S)-endo-norborneol is not obtained in equal purity (87.2% e.e.). That is, conventionally, it was not possible to obtain various high purity optically active isomers.

Further, the above (±)-3-[3-[(1RS,2RS,4SR)-bicyclo[2.2.1]hept-2-yloxy]-4-methoxyanilino]-2-methyl-2-cyclopenten-1-one does not have functional groups exhibiting acidity or basicity. It was not possible to employ optical separation using the technique of diastereomer utilizing optically active organic bases or organic acids for the separation. Therefore the differences in the PDE IV inhibitory activity and the side effects of those compounds were not known and could not be studied.

The inventors engaged in further research to obtain pure isomers and, as a result, found the method of separating (±)-3-[3-[(1RS,2RS,4SR)-bicyclo[2.2.1]hept-2-yloxy]-4-methoxyanilino]-2-methyl-2-cyclopenten-1-one into pure isomers by high performance liquid chromatography. We studied the PDE IV inhibitory activity and PDE III inhibitory activity of each isomer obtained, whereby the present invention has been completed.

That is, in accordance with the present invention, there is provided (−)-3-[3-[(1R,2R,4S)-bicyclo[2.2.1]hept-2-yloxy]-4-methoxyanilino]-2-methyl-2-cyclopenten-1-one, or its hydrate or solvate.

In accordance with the present invention, there is also provided a pharmaceutical composition comprising (−)-3-[3-[(1R,2R,4S)-bicyclo[2.2.1]hept-2-yloxy]-4-methoxyanilino]-2-methyl-2-cyclopenten-1-one, or its hydrate or solvate.

MODE FOR CARRYING OUT THE INVENTION

The present invention will be described in detail as below. Note that in the description and the claims, the singular form shall also include the plural form unless it is clearly singular from the context.

The optically active pure compound of the present invention is obtained by treating the racemate produced by the method described in, for example, Japanese Unexamined Patent Publication (Kokai) No. 11-189577 using high performance liquid chromatography (HPLC)under specific conditions, as described in the following Examples, so as to separate the racemate into two optically active isomers (i.e., (−)-3-[3-[(1R,2R,4S)-bicyclo[2.2.1]hept-2-yloxy]-4-methoxyanilino]-2-methyl-2-cyclopenten-1-one and (+)-3-[3-[(1S,2S,4R)-bicyclo[2.2.1]hept-2-yloxy]-4-methoxyanilino]-2-methyl-2-cyclopenten-1-one). Further, the optically active isomers obtained may be further made into optically active isomers having a high purity, if necessary, by recrystallization with various solvents.

Recrystallization can be performed using methanol, ethanol, isopropanol, butanol, acetone, ethyl acetate, chloroform, n-hexane, cyclohexane, water, etc., alone or a combined mixed solvent of two or more solvents.

The inhibitory activity of PDE IV and PDE III of the optically active (−)-isomer [abbreviation for (−)-3-[3-[(1R,2R,4S)-bicyclo[2.2.1]hept-2-yloxy]-4-methoxyanilino]-2-methyl-2-cyclopenten-1-one] and (+)-isomer [abbreviation for (+)-3-[3-[(1S,2S,4R)-bicyclo[2.2.1]hept-2-yloxy-4-methoxyanilino]-2-methyl-2-cyclopenten-1-one] obtained by the above method are shown in the Tables, compared with that of the racemate [(±)-isomer]. Table 1 summarizes the results of the Test Example 1 explained below.

TABLE I

| | Name of compound | | |
|---|---|---|---|
| | (−)-isomer | (±)-isomer | (+)-isomer |
| PDE IV inhibitory activity $IC_{50}$ value ($\mu$M) | 0.12 | 0.27 | 0.36 |
| PDE III inhibitory activity $IC_{50}$ value ($\mu$M) | 9.03 | 3.86 | 1.57 |

As shown in the above Table, the (−)-isomer has a PDE IV inhibitory activity of about twice that of the racemate and a PDE III inhibitory activity of less than half of that of the racemate. Compared with the racemate, the selectivity with respect to PDE IV is high. On the other hand, the (+)-isomer has a PDE IV inhibitory activity of about ¾ of that of the racemate and a PDE III inhibitory activity of twice or more of that of the racemate. The selectivity with respect to PDE IV is low. Further, the PDE III inhibitory activity strongly expressed in the racemate exhibits undesirable side effects on the system of circulation and, therefore, is not desirable. Therefore, the (−)-isomer has a strong main effect and weak side effects, compared with the racemate. This is the superior effect of the present invention. It was confirmed that the compound is extremely useful as a PDE IV inhibitor, compared with the racemate.

When the compound of the present invention is used for a therapeutic agent, the optically active compound obtained by the above method, or its hydrate or solvate can be administered alone or together with a pharmaceutically acceptable vehicle.

In the case of systemic administration, the compound may be orally administered in the form of granules, powders, tablets, pills, hard capsules, soft capsules, syrups, emulsions, suspensions, liquids, etc. or may be administered by non-oral route such as an injection (intravenous, intramuscular, subcutaneous), an ointments, suppositories or aerosols. In the case of topical administration, the compound may be used in the form of ointments, suppositories, or aerosols, etc.

Note that the preparation, as desired or if necessary, may also have added to it various additives usually used, when making a preparation, such as a suitable binder, lubricant, disintegrant, preservative, buffer, thickener, solution adjuvant, chelating agent, stabilizer, pH adjuster, or isotonic agent.

For example, in the case of an oral drug, excipients such as lactose, crystalline cellulose, glucose, corn starch, sucrose, sorbitol, mannitol, erythritol; disintegrants such as calcium carboxymethylcellulose, hydroxypropylcellulose; lubricants such as calcium stearate, magnesium stearate, talc, polyethylene glycol, hydrogenated oil; humectants such as hydroxypropylcellulose, hydroxypropylmethylcellulose, carboxymethylcellulose, polyvinyl alcohol, gelatin, gum arabic; and also, if necessary, a surfactant, flavoring agents, etc. may be used to prepare the desired form of administration.

Further, in the case of a non-oral drug, a diluent such as water, ethanol, glycerin, propyleneglycol, polyethyleneglycol, agar, gum tragacanth may be used, if necessary, with a solution adjuvant (e.g., polyvinylpyrrolidone, polyoxyethylene hydrogenated castor oil, polyethylene glycol, Polysorbate 80 (Trade Mark), polyoxyethylene monostearate, etc.), preservative (e.g., chlorobutanol, sodium dehydroacetate, benzalkonium chloride, cetylpyridium chloride, phenetyl alcohol, p-oxybenzoate esters, benzethonium chloride, etc.), buffer (e.g., borate buffer, phosphate buffer, carbonate buffer, acetate buffer, citrate buffer, etc.), pH adjuster (e.g., sodium hydroxide, potassium hydroxide, sodium carbonate, sodium bicarbonate, acetic acid, citric acid, phosphoric acid, etc.), isotonic agent (e.g., sodium chloride, potassium chloride, glycerin, polyhydric alcohol, sorbitol, mannitol, glucose, etc.), soothing agents, etc. may be used.

The clinical dosage of the compound according to the present invention, in the case of oral administration as a preparation for systemic administration, is usually 0.01–1000 mg per day, preferably 0.01–100 mg, for an adult. The dosage is preferably suitably adjusted depending upon age, condition, symptoms, existence of co-administration, etc. The daily amount of the medicine (i.e., the compound of the present invention) may be administered once a day or divided into two or more dosages at suitable intervals or may be administered intermittently. Further, when used as an injection for systemic administration, as the compound of the present invention, it is preferable to administer a dosage of 0.001–100 mg for an adult continuously or intermittently.

The clinical dosage when topically administering the compound of the present invention, in the case of an inhalant, is usually 0.001–300 mg per day, preferably 0.001–30 mg, for an adult. The dosage is preferably suitably adjusted depending upon age, condition, symptoms, existence of co-administration, etc. In the case of an injection, the compound is administered divided into several dosages per day. Further, when used as an external agent, for an adult, the compound of the present invention is applied on the affected location several times a day by a substrate containing 0.01–1.0%, but this is preferably suitably adjusted depending upon age, condition, symptoms, existence of co-administration, etc.

EXAMPLES

The present invention will now be described in detail by Examples and Test Examples, but the present invention is not limited to these Examples and Test Examples in so far as its gist is not exceeded.

Example 1

(±)-3-[3-[(1RS,2RS,4SR)-bicyclo[2.2.1]hept-2-yloxy]-4-methoxyanilino]-2-methyl-2-cyclopenten-1-one in an amount of 1.8 g was dissolved in 1.8 liters of a mobile phase, then a sample solution of about 70 mg was injected all at once into a column for HPLC (i.e., high performance liquid chromatography) under the following conditions.

Column: CHIRALCEL OD (10 cmφ×50 cm)

Mobile phase: n-hexane/isopropanol/diethyl amine=90/10/0.1

Flow rate: 190 mL/min.

The fractions of the first peak and the second peak were concentrated in vacuo to obtain an oily residue. Ethanol and n-hexane were then added thereto, then the resultant mixture was again concentrated in vacuo to obtain a powdery optically active isomer. By repeating the above operation, two types of optically active isomers, that is, the (−)-isomer and (+)-isomer, were obtained in amounts of 0.70 g and 0.64 g, respectively, from 1.8 g of (±)-3-[3-[(1RS,2RS,4SR)-bicyclo[2.2.1]hept-2-yloxy]-4-methoxyanilino]-2-methyl-2-cyclopenten-1-one. Further, the structures of the optically active isomers were confirmed by comparison with the NMR of the racemate.

(−)-isomer: retention time 86–98 minutes, column temperature 40° C.

$[\alpha]^{20}_D$ −19° (c=1.00,EtOH)

$^1$H-NMR(400 MHz, CDCl$_3$)δ(ppm)1.12–1.18(2H, m), 1.21–1.23(1H, m), 1.48–1.54(1H, m), 1.56–1.64(2H, m), 1.68(3H, s), 1.72–1.80(2H, m), 2.35(1H, m), 2.39–2.41(2H, m), 2.51(1H, d, J=4.39 Hz), 2.55–2.56(2H, m), 3.85(3H, s), 4.16–4.17(1H, m), 6.41(1H, broad s), 6.65(1H, d, J=2.44 Hz), 6.69(1H, dd, J=8.79,2.44 Hz), 6.83(1H, d, J=8.79 Hz)

(+)-isomer: retention time 103–121 minutes, column temperature 40° C.

$[\alpha]^{20}_D$ +19° (c=1.00, EtOH)

(±)-isomer $^1$H-NMR(400 MHz, CDCl$_3$)δ(ppm)
1.12–1.18(2H, m), 1.21–1.23(1H, m), 1.48–1.54(1H, m), 1.56–1.64(2H, m), 1.68(3H, s), 1.72–1.80(2H, m), 2.35(1H, m), 2.39–2.41(2H, m), 2.51(1H, d, J=4.39 Hz), 2.55–2.56 (2H, m), 3.85(3H, s), 4.16–4.17(1H, m), 6.47(1H, broad s), 6.65(1H, d, J=2.44 Hz), 6.69(1H, dd, J=8.79,2.44 Hz), 6.83(1H, d, J=8.79 Hz).

Example 2

Preparation of Tablet 30 g of (−)-3-[3-[(1R,2R,4S)-bicyclo[2.2.1]hept-2-yloxy]-4-methoxyanilino]-2-methyl-2-cyclopenten-1-one, lactose 253 g, corn starch 63 g, low substituted hydroxypropylcellulose 40 g, and calcium stearate 4 g were mixed and compressed by an ordinary method to prepare tablets containing the above compound in an amount of 10 mg.

Example 3

Preparation of Capsule 30 g of (−)-3-[3-[(1R,2R,4S)-bicyclo[2.2.1]hept-2-yloxy]-4-methoxyanilino]-2-methyl-2-cyclopenten-1-one, lactose 260 g, corn starch 66 g, and calcium stearate 4 g were mixed, then filled into gelatin capsules by an ordinary method to produce capsules containing the above compound in an amount of 10 mg.

Example 4

Preparation of Inhalant (−)-3-[3-[(1R,2R,4S)-bicyclo[2.2.1]hept-2-yloxy]-4-methoxyanilino]-2-methyl-2-cyclopenten-1-one was pulverized well to a particle size of 1–5 μm. 0.15 g of this and 60 g of lactose (325 mesh, made by DMV) were mixed. The mixture was filled in capsules by an ordinary method so that each capsule contained the above compound in an amount of 50 μg. Inhalation was performed by loading a capsule in a powder inhalation container.

Example 5

Production of Ointment 100 mg of (−)-3-[3-[(1R,2R,4S)-bicyclo[2.2.1]hept-2-yloxy]-4-methoxyanilino]-2-methyl-2-cyclopenten-1-one, olive oil 20 g, and white vaseline 79.9 g were mixed under sterile conditions to prepare an ointment.

Test Example 1

Separation of Phosphodiesterase (PDE)and Measurement of PDE Inhibiting Activity

To investigate the PDE inhibitory activity and selectivity of the compound, Type I, Type III, Type IV and Type V, that is, four types of PDE isozymes were prepared *Trends Pharmacol. Sci.* (*TiPS*), vol. 12, 19–27(1991). The Type I PDE used was one purchased from Sigma. Further, the Type III, Type IV and Type V PDE isozymes used were those partially purified from the blood platelets (Type III and Type V) or neutrophils (Type IV) taken from rats. Each enzyme source was homogenized in a buffer (pH6.5) containing 20 mM Bis-Tris, EDTA (ethylene diamine tetraacetate) 2 mM, PMSF (phenylmethylsulfonyl fluoride) 0.1 mM, 2-mercaptoethanol 5 mM, pepstatin 0.001 mM, and leupeptin 0.01 mM and centrifuged at 30000×G for 30 minutes. The centrifuged supernatent was passed through an ion exchange column (Q Sepharose Fast Flow, made by Pharmacia) and eluted by 0–1M sodium acetate. The partially purified isozyme was identified by investigating the effects of known selective inhibitors.

The tested compound was dissolved in DMSO (dimethylsulfoxide) and added to 50 mM tris-HCl buffer containing 5 mM magnesium hydrochloride. To this reaction solution, the above PDE isozyme and $^3$H-cAMP (when Type III or Type IV of PDE) or $^3$H-cGMP (when Type I or Type V of PDE) was added, as a substrate, and the mixture reacted at 30° C. for 30 minutes. After the reaction, the reaction mixture was placed in a 100° C. boiling solution for 5 minutes to stop the reaction. The nucleotide produced by the PDE was decomposed by 5'-nucleotidase into $^3$H-adenosine or $^3$H-guanosine. The unreacted substrate and reaction product were passed through an ion exchange column (QAE Sephadex, made by Pharmacia)to separate them. The radioactivity of the eluted $^3$H-nucleoside was measured by a liquid sintillation counter. The inhibitory activity of each tested compound was indicated by the IC$_{50}$ value (μM). The inhibitory activity against Type IV was shown in Table 2, while the inhibitory activity against Type III was shown in Table 3. Further, the inhibitory activity of each test compound to Type I and Type V was less than 1/10 to Type IV.

TABLE II

PDE IV Inhibitory Activity

| Name of compound | IC$_{50}$ value (μM). |
| --- | --- |
| (−)-isomer | 0.12 |
| (±)-isomer | 0.27 |
| (+)-isomer | 0.36 |

TABLE III

PDE III Inhibitory Activity

| Name of compound | IC$_{50}$ value (μM). |
| --- | --- |
| (−)-isomer | 9.03 |
| (±)-isomer | 3.86 |
| (+)-isomer | 1.57 |

Industrial Applicability

The compound of the present invention has a strong PDE IV inhibitory activity of at least two times that of a racemate and has a PDE III inhibitory activity exhibiting undesirable side effects on the circulatory system less than ½ of that of a racemate, so is extremely useful for the treatment of inflammatory diseases such as asthma, dermatitis.

What is claimed is:

1. An at least 95% enantiomeric excess of (−)-3-[3-[(1R, 2R,4S)-bicyclo[2.2.1]hept-2-yloxy]-4-methoxyanilino]-2-methyl-2-cyclopenten-1-one, or its hydrate or solvate.

2. A pharmaceutical composition, comprising: an at least 95% enantiomeric excess of (−)-3-[3-[(1R,2R,4S)-bicyclo [2.2.1]hept-2-yloxy]-4-methoxyanilino]-2-methyl-2-cyclopenten-1-one, or its hydrate or solvate, combined with a pharmaceutically acceptable vehicle.

3. A Pharmaceutical composition as recited in claim 2, further comprising one or more of an additive, excipient, or diluent.

4. A pharmaceutical composition as recited in claim 2, wherein the composition is suitable for oral administration.

5. A pharmaceutical composition as recited in claim 2, wherein the composition is suitable for administration by injection.

6. A pharmaceutical composition as recited in claim 2, wherein the composition is suitable for topical administration.

7. A pharmaceutical composition as recited in claim 2, wherein the composition is suitable for administration by inhalation.

8. A method of treating a patient suffering from dermatitis, atopic dermatitis, contact dermatitis, urticaria, or psoriasis, comprising: administering to the patient a therapeutically effective dose of a pharmaceutical composition as recited in claim 2.

9. A method of treating a patient suffering from asthma or chronic obstructive pulmonary disease, comprising: administering to the patient a therapeutically effective dose of a pharmaceutical composition as recited in claim 2.

10. A method of treating a patient suffering from dermatitis, atopic dermatitis, contact dermatitis, urticaria, or psoriasis, comprising: administering to the patient a therapeutically effective dose of an at least 95% enantomeric excess of (−)-3-[3-[(1R,2R,4S)-bicyclo[2.2.1]hept-2-yloxy]-4-methoxyanilino]-2-methyl-2-cyclopenten-1-one, or its hydrate or solvate.

11. A method of treating a patient suffering from asthma or chronic obstructive pulmonary disease, comprising: administering to the patient a therapeutically effective dose of an at least 95% enantomeric excess of (−)-3-[3-[(1R,2R,4S)-bicyclo[2.2.1]hept-2-yloxy]-4-methoxyanilino]-2-methyl-2-cyclopenten-1-one, or its hydrate or solvate.

* * * * *